(12) United States Patent
Levy et al.

(10) Patent No.: US 10,448,998 B2
(45) Date of Patent: Oct. 22, 2019

(54) LASER TREATMENT APPARATUS

(71) Applicant: LUMENIS LTD., Yokneam Ilit (IL)

(72) Inventors: Shaul Levy, Yokneam Ilit (IL); Igor Igal Koifman, Yokneam Ilit (IL); Uri Voitsechov, Yokneam Ilit (IL)

(73) Assignee: LUMENIS LTD. (IL)

( * ) Notice: Subject to any disclaimer, the term of this patent is extended or adjusted under 35 U.S.C. 154(b) by 289 days.

(21) Appl. No.: 15/089,672

(22) Filed: Apr. 4, 2016

(65) Prior Publication Data

US 2016/0213427 A1  Jul. 28, 2016

Related U.S. Application Data

(63) Continuation of application No. PCT/IB2014/065112, filed on Oct. 7, 2014.

(51) Int. Cl.
*A61B 18/20* (2006.01)
*A61N 5/06* (2006.01)
*A61B 18/00* (2006.01)
*A61N 5/00* (2006.01)
*A61N 5/067* (2006.01)

(52) U.S. Cl.
CPC .......... *A61B 18/203* (2013.01); *A61N 5/0616* (2013.01); *A61B 2018/00023* (2013.01); *A61B 2018/00452* (2013.01); *A61B 2018/202* (2013.01); *A61B 2018/2023* (2017.05); *A61N 2005/005* (2013.01); *A61N 2005/067* (2013.01); *A61N 2005/0644* (2013.01)

(58) Field of Classification Search
CPC ........ A61B 18/203; A61B 2017/00464; A61B 2017/00473; A61B 2018/00023; A61B 2018/00452–00476; A61B 2018/00231; A61B 2018/00262; A61B 2018/202; A61B 2018/2253; A61B 2018/2285; A61N 5/0616; A61N 2005/005; A61N 2005/0644; A61N 2005/067
USPC ....................................................... 606/9–18
See application file for complete search history.

(56) References Cited

U.S. PATENT DOCUMENTS 5,728,090 A * 3/1998 Martin ................. A61N 5/0601
606/11
2007/0198004 A1   8/2007 Altshuler et al.

FOREIGN PATENT DOCUMENTS

KR   20120073070   7/2012
WO   2007007167    1/2007
WO   2008012519    1/2008

* cited by examiner

*Primary Examiner* — Eugene T Wu
(74) *Attorney, Agent, or Firm* — Isus Intellectual Property PLLC

(57) ABSTRACT

A laser treatment apparatus comprising a primary handset, the primary handset being connectable to an auxiliary attachment, the primary handset having a laser source having a primary heat exchanger, and a cooling circuit to provide cooling fluid to the primary heat exchanger to cool the laser source, the cooling circuit having an auxiliary circuit connection, for engagement with an auxiliary attachment.

4 Claims, 9 Drawing Sheets

LASER TREATMENT APPARATUS

RELATED APPLICATIONS

This application is a continuation application of PCT Application Serial No. PCT/IB32014/065112, filed Oct. 8, 2014, which claims priority to Great Britain Patent Application No. 1317752.2, filed Oct. 8, 2013

FIELD OF THE INVENTION

This application relates to a laser treatment apparatus having a primary handset, an auxiliary attachment for a primary handset of a laser treatment apparatus, a laser treatment system having a primary handset and at least one auxiliary attachment, and a primary handset for a laser treatment apparatus.

BACKGROUND TO THE INVENTION

Lasers are used for a large number of aesthetic and cosmetic treatments, such as hair removal, skin pigmentation treatment and vein treatment. Using lasers provides a fast and straightforward treatment process. Most of the common applicators in laser treatment use integral cooling of the treatment device tip to reduce the risk of skin burns and in addition reduce patient discomfort. A disadvantage of such laser treatment systems is that the systems have specific optical characteristics, such as treatment area, spot size and laser wavelength, and are not easily adaptable. Also, this type of applicator cannot be used with other application techniques, such as a vacuum tip. It is known to provide a single apparatus with two or more handsets to provide different treatment characteristics, but this may not provide the desired flexibility and is not cost-effective.

SUMMARY OF THE INVENTION

According a first aspect of the invention there is provided a laser treatment apparatus comprising a primary handset, the primary handset being connectable to an auxiliary attachment, the primary handset having a laser source having a primary heat exchanger, and a cooling circuit to provide cooling fluid to the primary heat exchanger to cool the laser source, the cooling circuit having an auxiliary circuit connection, for engagement with an auxiliary attachment.

The cooling circuit may have a main loop connected to the primary heat exchanger, the auxiliary cooling circuit connection being connected to the main loop.

The auxiliary circuit connection may comprise a fluid connection for connection to a cooling duct of the auxiliary handset.

The auxiliary circuit connection may alternatively comprise an auxiliary loop connected to the main loop.

The auxiliary cooling loop may have an auxiliary heat exchanger, for engagement with an auxiliary attachment.

The laser treatment apparatus may further comprise a main loop valve, the main loop valve being operable to permit cooling fluid to flow in the main loop when no auxiliary attachment is connected, and to enforce fluid diversion to the auxiliary loop when an auxiliary attachment is connected.

The main loop valve may comprise a uni-directional valve.

The laser treatment apparatus may comprise a pump to pump cooling fluid around the cooling circuit.

The laser treatment apparatus may comprise a switching valve to controllably direct fluid around the cooling circuit in a first direction when no auxiliary attachment is connected such that fluid passes through the valve and in a second direction when an auxiliary attachment is connected such that fluid does not pass through the valve.

Alternatively, the pump may be operable to pump fluid in a first direction when no auxiliary attachment is connected such that fluid passes through the valve and in a second direction when an auxiliary attachment is connected such that fluid does not pass through the valve.

According to a second aspect of the invention there is provided an auxiliary attachment for connection to a primary handset of a laser treatment apparatus, the auxiliary attachment having a forward window to transmit laser light from the primary handset, and an attachment cooling circuit to provide cooling fluid to cool the forward window, the cooling circuit being connected to an attachment heat exchanger, the heat exchanger being connectable to an auxiliary circuit connection of the primary handset.

The auxiliary attachment may comprise a cooling duct in contact with the attachment heat exchanger, the cooling duct being connectable to the auxiliary circuit connection.

Alternatively the heat exchanger may be arranged to engage an auxiliary heat exchanger of a primary handset The auxiliary attachment may further comprise a pump to pump cooling fluid around the attachment cooling circuit.

According to a third aspect of the invention there is provided a laser treatment system, the laser treatment system comprising a laser treatment apparatus according to the first aspect of the invention and at least one auxiliary attachment according to the second aspect of the invention.

The laser treatment system may comprise a plurality of auxiliary attachments, such that each auxiliary attachment is selectively connectable to and releasable from the primary handset.

According to a fourth aspect of the invention there is provided a laser treatment system comprising a primary handset and a plurality of auxiliary attachments releasably connectable to the primary attachment, the system further comprising an attachment tray, the attachment tray comprising a plurality of holders, each holder adapted to receive a corresponding auxiliary attachment.

Each holder may have an associated release mechanism, and the auxiliary attachment may be connected to the primary handset by a latch mechanism, whereby the latch mechanism may be releasable by the release mechanism when the auxiliary attachment is located in the corresponding holder.

The auxiliary attachment may only be released from the primary handset when the auxiliary attachment is located in the corresponding holder.

The laser treatment system may comprises a laser treatment system according the third aspect of the invention.

According to a fifth aspect of the invention there is provided a primary handset for a laser treatment system, the primary handset having an umbilical connection to for connection to a base station, the primary handset being connected to the umbilical connection by a rotating joint, the rotating joint being movable between a central latched position and at least one offset latched position rotatably offset from the central latched position.

The rotating joint may be movable between a central latched position and two offset latched positions disposed one on either side of the central latched position and offset therefrom.

BRIEF DESCRIPTION OF THE DRAWINGS

An embodiment of the invention is described by way of example only with reference to the accompanying drawings, wherein;

FIG. 2d is an illustration of an alternative embodiment of the cooling circuit of FIG. 2a.

DETAILED DESCRIPTION OF THE PREFERRED EMBODIMENTS

Figure 1B:
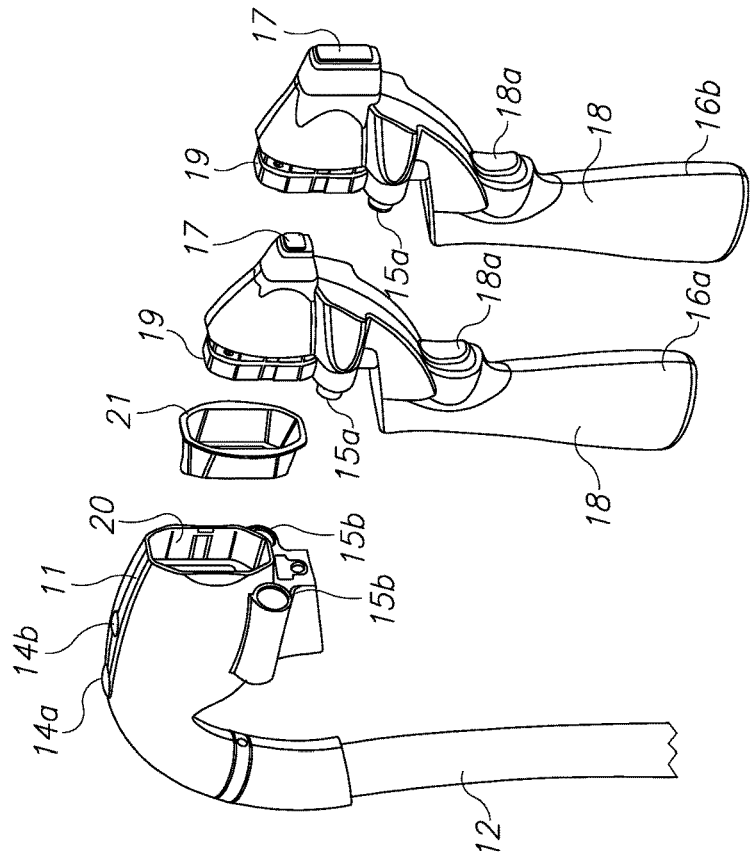
FIG. 1b shows a primary handset with detached alternative attachments.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1A:
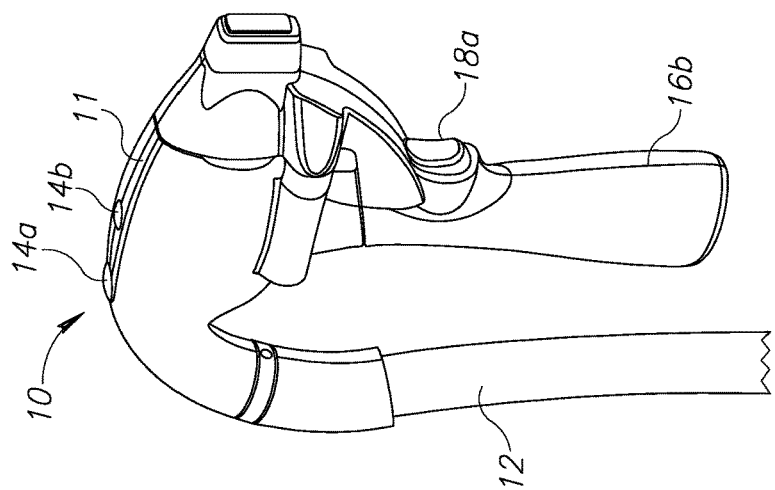
FIG. 1a shows a primary handset and connected auxiliary attachment.
Figure 2A:
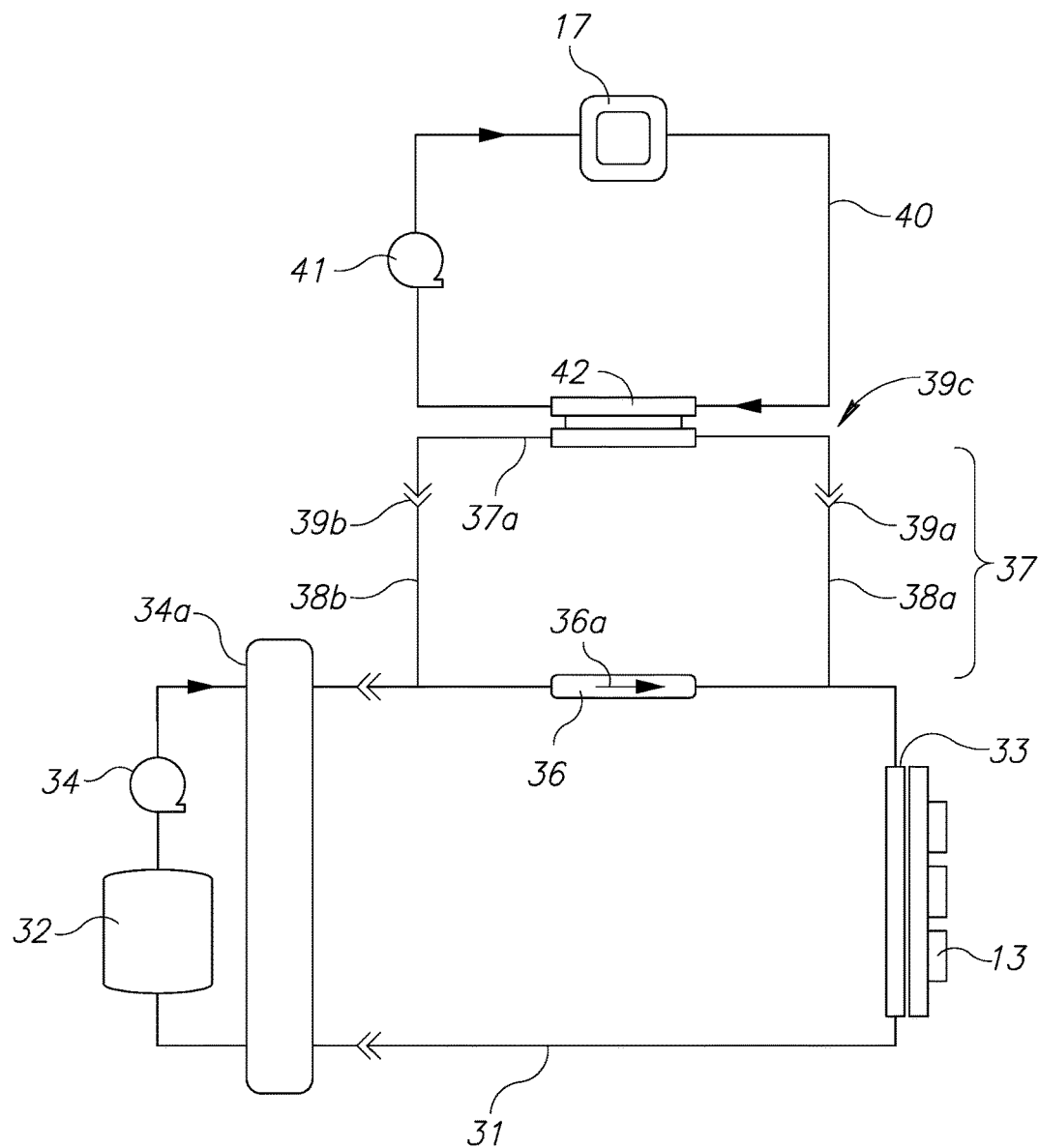
FIG. 2a is an illustration of the cooling circuit of the primary handset and auxiliary attachment.

Referring now to Figs 1a and 1b, a laser treatment apparatus is generally shown at 10. The apparatus 10 comprises a primary handset 11. The primary handset 11 is connected to a base unit (not shown) by an umbilical connection 12, for example to provide a power connection, and connection to a control panel where the operator may set the treatment parameters. The primary handset 11 has a laser source comprising one or more laser diodes 13, as shown in FIG. 2a, and a pair of operator controls shown at 14a, 14b.

The primary handset 11 may be used separately, or with an auxiliary attachment. Auxiliary attachments with small and large tip sizes are shown at 16a and 16b respectively. The auxiliary attachments 16a, 16b are releasably connectable to the primary handset 11 by a latch mechanism, in this example comprising projections 15a on the auxiliary attachment 16a, 16b received in connectors 15b provided on the primary handset 11. The engagement of the projections 15a and connections 15b holds the primary handset 11 and auxiliary attachment 16a, 16b firmly in the correct orientation. An auxiliary attachment 16b is shown connected to the primary handset 11 in FIG. 1a.

Each auxiliary attachment may be configured to have a different treatment area or cone size, so that laser light can be concentrated in a specific treatment area. The auxiliary attachments have a tip window 17, which is cooled as described below to reduce patient discomfort. In addition, each auxiliary attachment has a handle 18, to allow an operator to position and control the apparatus 10, with an auxiliary control 18a provided on the handle 18, in this example in the form of a trigger.

A connecting sleeve 19 extends from an upper part of the auxiliary attachment 16a, 16b and is received in mouth 20 of the primary handset 11. The connecting sleeve 19 and mouth 20 interfit to provide a secure connection, such that laser light cannot escape from the connection between the primary handset 11 and auxiliary attachment 15, 16.

Where the primary handset 11 is used without an auxiliary attachment, a disposable insert 21 may be inserted into the mouth 20 for use with a vacuum system (not shown). The insert 21 will be located against the patient's skin and a vacuum formed within in the insert to draw tissue into the insert. For hygiene, insert 21 is discarded after use.

To provide for cooling of the laser diodes 13 and an auxiliary attachment 16a, 16b (when connected), a cooling apparatus is provided as generally shown at 30 in FIG. 2a. A cooling circuit 31 is provided in the primary handset 11, to provide cooling fluid from a reservoir 32 to a primary heat exchanger 33 to cool the laser diodes 13. A pump 34 is provided to pump cooling fluid from the reservoir 32 around the cooling circuit 31. The pump 34 is operable to pump cooling fluid in one direction, in this example clockwise away from the reservoir. To direct the flow of cooling fluid around the cooling circuit 31 in either of a first, clockwise direction or a second, anticlockwise direction, a switch valve 34a is connected between the pump 34 and reservoir 32, and the cooling circuit 31. The cooling circuit 31 has a main loop 35, extending from the reservoir 32, through pump 34, through main loop valve 36, to primary heat exchanger 33 and back to reservoir 32. In the present example main loop valve 36 comprises a uni-directional valve as shown by arrow 36a.

The auxiliary attachment 16a, 16b is provided with an attachment cooling circuit 40. Attachment cooling circuit 40 comprises a closed loop filled with cooling fluid pumped around the loop by pump 41. The attachment cooling circuit passes cooling fluid from attachment heat exchanger 42 to window 17, to cool the window.

Figure 2B:
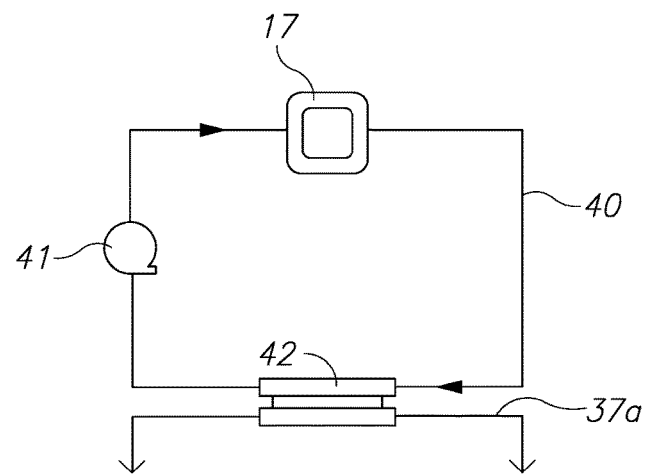
FIG. 2b is an illustration of the operation of cooling circuit of FIG. 2a where no auxiliary attachment is attached to the primary handset.
Figure 2B:
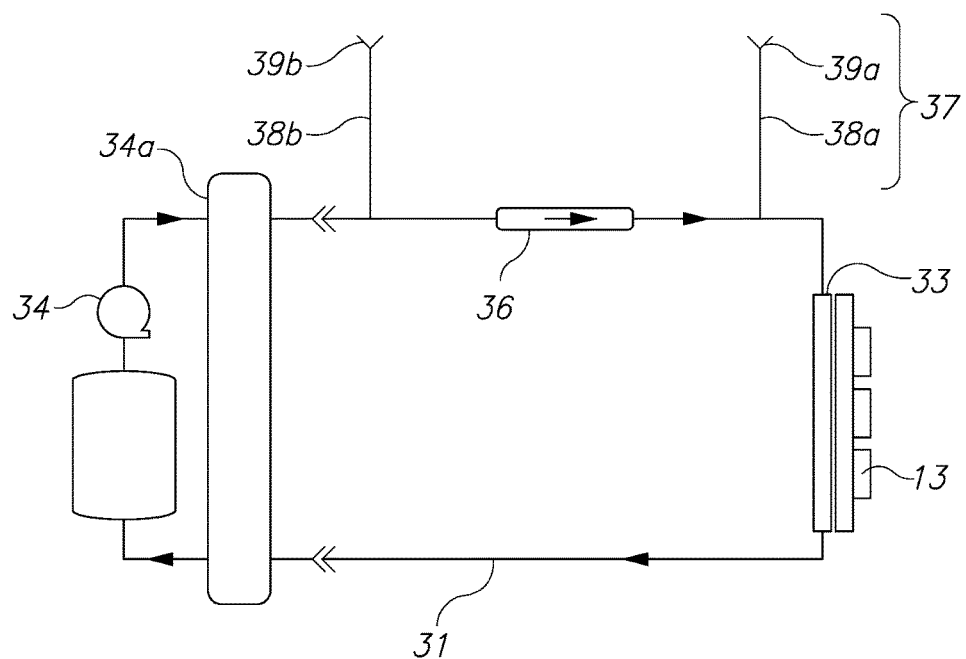

To provide for heat exchange with the attachment heat exchanger 42, an auxiliary circuit connection is provided, generally shown at 37. In the embodiment of FIGS. 2a and 2b, the auxiliary attachment has a cooling duct 37a in communication with attachment heat exchanger 42. The auxiliary circuit connection 37 further comprises first branch 38a and second branch 38b connected to main loop 35 either side of the main loop valve 36. Quick release fluid connectors 39a, 39b are provided to connect the cooling duct 37a to first and second branches 38a, 38b in fluid communication, thus defining an auxiliary loop 39c.

When no auxiliary attachment is connected to the primary handset 11, the cooling circuit functions as shown in FIG. 2b. As no auxiliary attachment is connected to fluid connectors 39a, 39b, first and second branches 38a, 38b are closed. Switch valve 34a is operated to pump fluid clockwise as shown by the arrows around the main loop 35, such that fluid passes through main loop valve 36 to primary heat exchanger 33. Accordingly, cooling is provided to laser diodes 13.

Figure 2C:
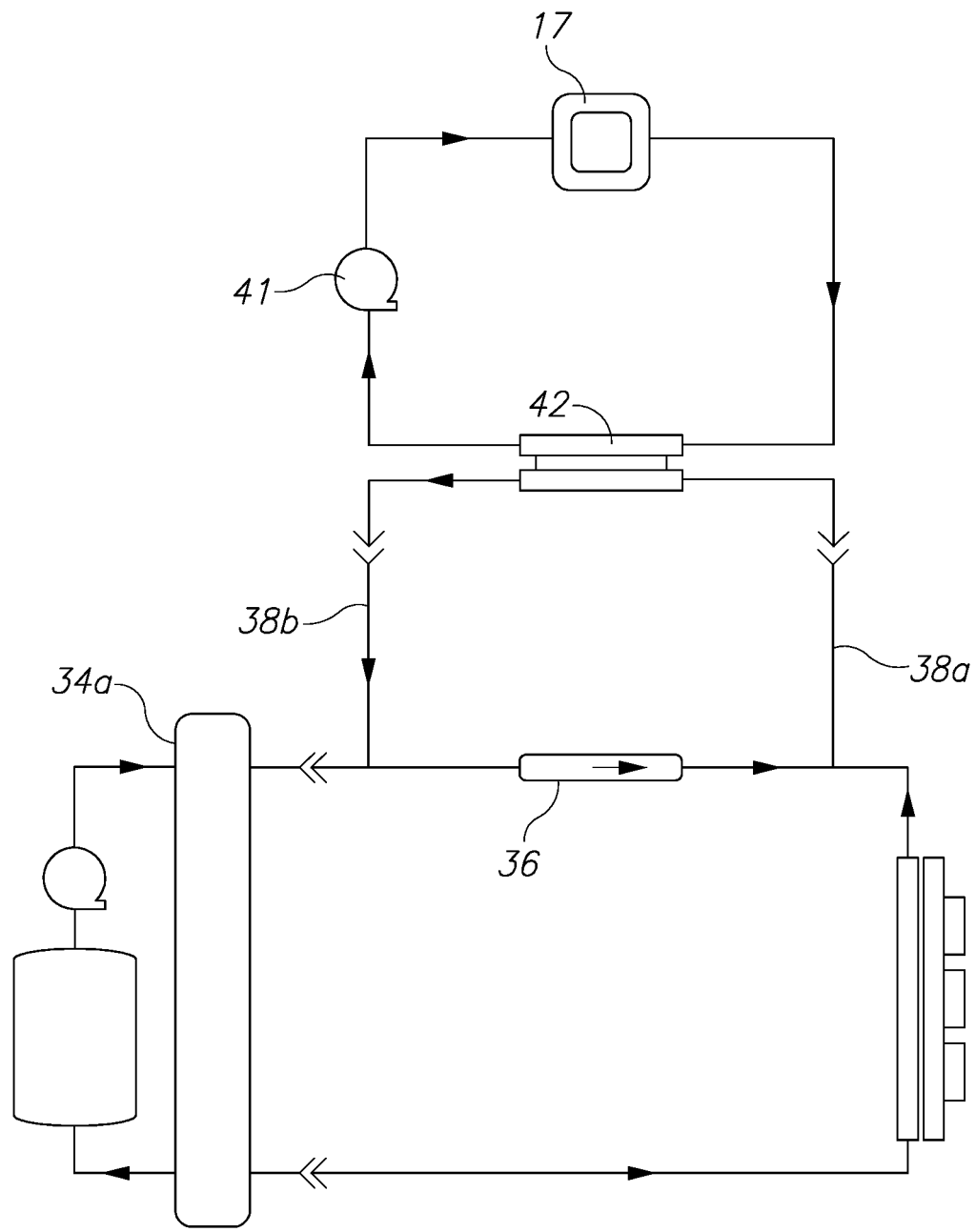
FIG. 2c is an illustration of the operation of the cooling circuit of FIG. 2a where an auxiliary attachment is attached to the primary handset.

When an auxiliary attachment is connected to the primary handset 11, the cooling circuit functions as shown in FIG. 2c. When an auxiliary attachment 15a, 15b is connected, first and second branches 38a, 38b and cooling duct 37a are in flow communication to define auxiliary loop 39c.

Switch valve 34a is operated to direct cooling fluid in an anticlockwise direction as shown in FIG. 2c. After passing through primary heat exchanger 33, the cooling fluid cannot pass through main loop valve 36, and accordingly all fluid is directed through auxiliary loop 39c through attachment heat exchanger 42. Pump 41 is operating to pass cooling fluid to cool window 17 and then to heat exchanger 42. The flow rate and cooling liquid volumes in the circuits 31. 40 are such that fluid passing through the cooling duct side of attachment heat exchanger 42 will be cooler than fluid passing through the attachment side of heat exchanger 42, thus cooling the fluid in the cooling circuit 40.

The arrangement of cooling circuits shown above thus allows multiple alternative attachments to be removably and interchangeably used with a single primary handset, while still provided cooling to the window or instrument tip to be placed against the patient's skin.

Figure 2D:
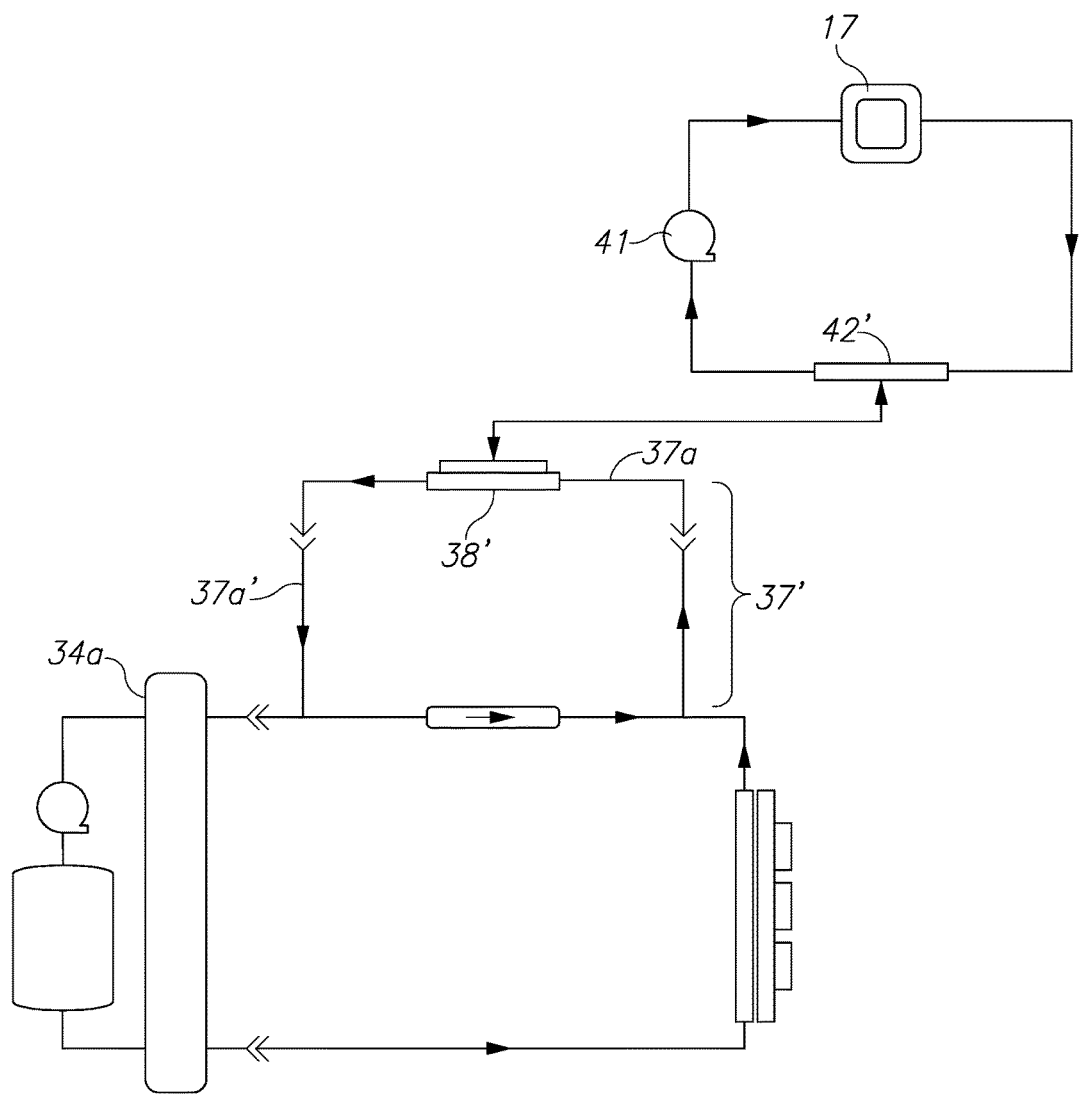

An alternative embodiment is shown in FIG. 2d. In this alternative, attachment cooling circuit 40 passes cooling fluid through attachment heat exchanger 42'. Auxiliary circuit connection 37' comprises a loop 37a' passing through secondary heat exchanger 38', such that secondary heat exchanger 38' is connected in parallel to main loop valve 36.

When no auxiliary attachment is connected to the primary handset 11, the cooling circuit functions as shown in FIG. 2b When an auxiliary attachment is connected to the primary handset 11, the cooling circuit functions as in a similar manner to the circuit of FIG. 2c. When an auxiliary attachment 16a, 16b is connected, heat exchangers 38', 42' are held in mutual contact, such that thermal transfer can occur between them. Pump 34 is operated to pump cooling fluid in an anticlockwise direction as shown in FIG. 2d. After passing through primary heat exchanger 33, the cooling fluid cannot pass through main loop valve 36, and accordingly all fluid is directed through secondary heat exchanger 38'. Pump 41 is operating to pass cooling fluid to cool window 17 and then to attachment heat exchanger 42'. The flow rate and cooling liquid volumes in the circuits 31. 40 are such that fluid passing through heat exchanger 38' will be cooler than fluid passing through heat exchanger 42', thus cooling the fluid in the attachment cooling circuit 40.

Figure 2E:
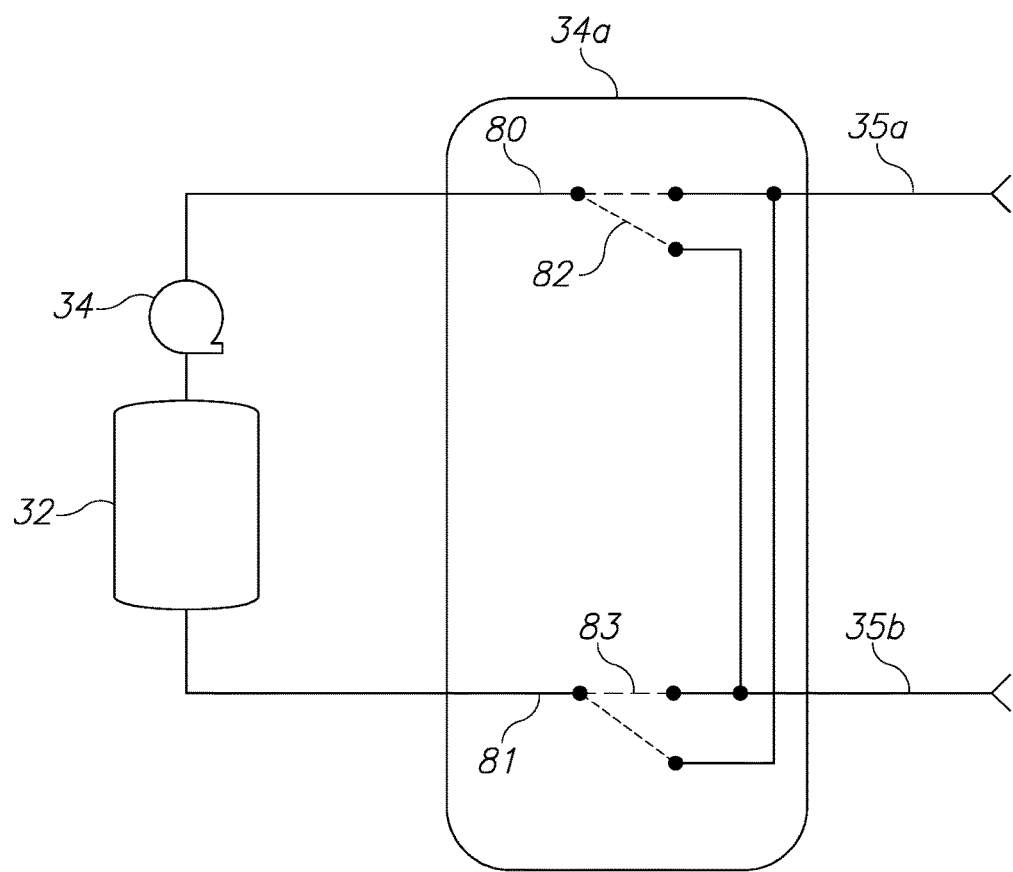
FIG. 2e is an illustration of a switching valve of the cooling circuit of FIG. 2a, FIG. 3a is a perspective view of a primary handset and auxiliary attachment in a holder.

An example of a switch valve 34a is shown in FIG. 2e. Pump 34 is connected to input line 80, and the reservoir 32 to return line 81. A first connection to main loop 35 is shown at 35a and a second connection to main loop 35 is shown at 35b. Coupled selector valves are shown at 82, 83. In a first position, selector valve 82 couples input line 80 to first connection 35a, and selector valve 83 couples second connection 35b to return line 81. In a second position, selector valve 82 couples input line 80 to second connection 35b, and selector valve 83 couples first connection 35a to return line 81. Accordingly, pump 34 is operable to pump cooling fluid in a single direction, clockwise in this diagram, and the switch valve 34a allows the cooling fluid to circulate in either direction around the main loop.

In a further alternative, if reservoir 32 is omitted, pump 34 may be operable to pump cooling fluid in both directions around cooling circuit 31, plus removing the need for switch valve 34a.

Figure 3B:
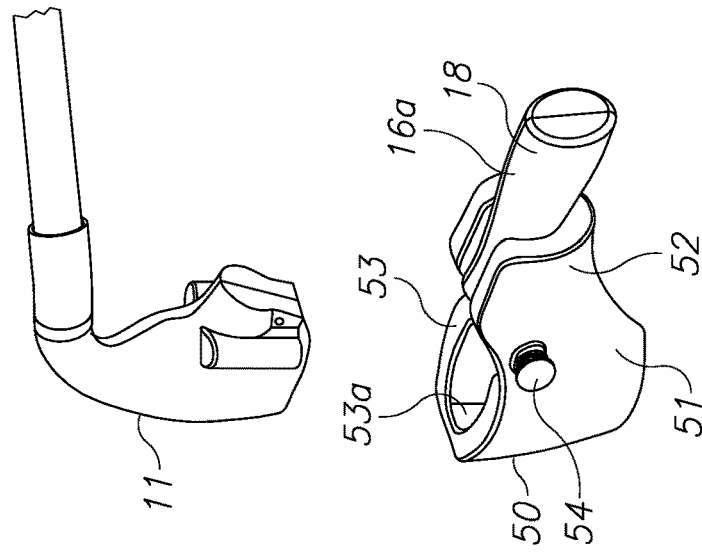
FIG. 3b is a similar view to FIG. 3b wherein the primary handset has been released from the auxiliary attachment.
Figure 3A:
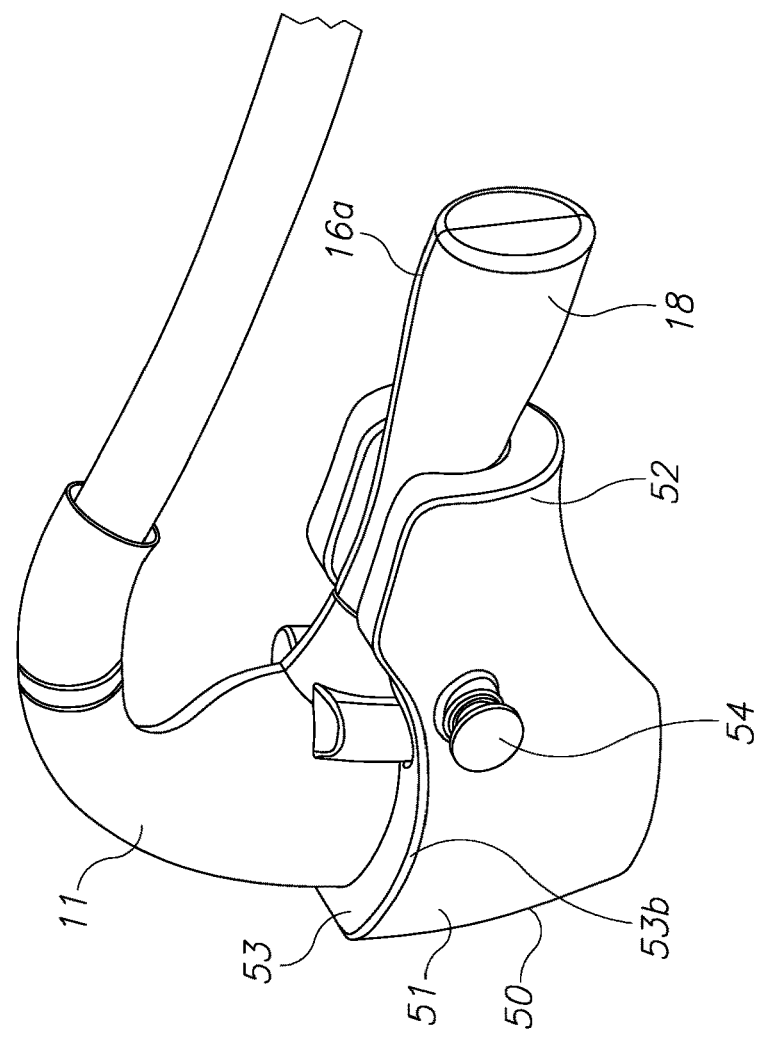

To hold the auxiliary attachments, the laser treatment system has a corresponding holder for each auxiliary attachment as shown in FIGS. 3a and 3b. The holder is shown at 50, comprising a bowl section 51 to receive the body of the auxiliary attachment and a side cradle 52 to receive the handle 18. As is apparent from the figures, an internal buffer 53 lines the inside of the holder and is shaped to snugly receive the auxiliary attachment 16a, 16b. In this example, internal buffer 53 has an internal cavity 53a which is configured to accept an auxiliary attachment and an external surface 53b configured to fit the interior of holder 50. Different internal buffers 53 can be configured to snugly receive different auxiliary attachments by having suitable internal cavity designs and a common external surface design so a universal holder 50 can be used to hold all auxiliary attachments.

A release button is shown at 54, which may be pressed to release the latch mechanism, enabling the primary handset 11 to be disconnected from the auxiliary attachment 16a, 16b as shown in FIG. 3b. The latch mechanism may be any suitable mechanism, but is preferably configured such that manual or accidental release (i.e., without using release button 54) is difficult, for example by making the latch mechanism difficult to access or resistant to release by other methods. This is advantageous in that the auxiliary attachments 15a, 15b cannot be accidentally released from the primary handset, or cannot be deliberately released and then left in an unsafe position, dropped or damaged. The holder 50 and release button 54 ensure that the primary handset and auxiliary attachment 16a, 16b can only be released when the auxiliary attachment is in its corresponding holder. Preferably, the laser treatment system will have a plurality of holders, each corresponding to one of a plurality of auxiliary attachments.

Figure 4A:
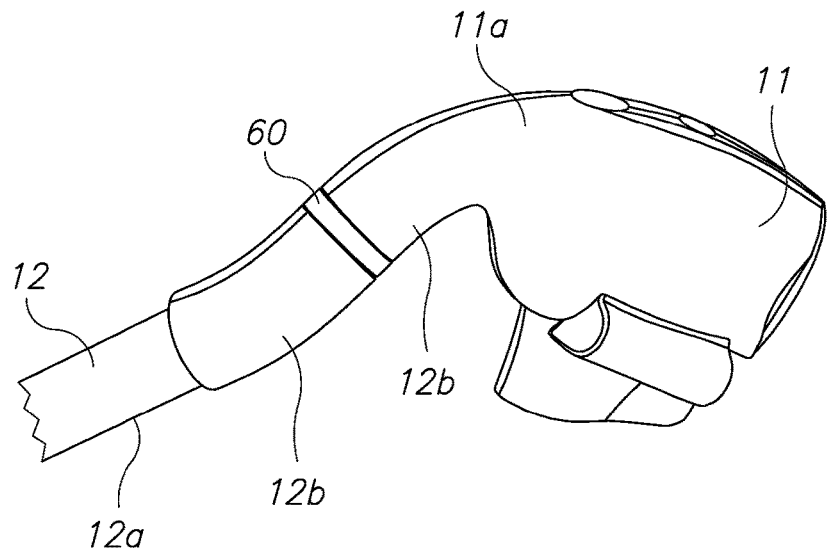
FIG. 4a is perspective view of a primary handset and umbilical connection showing a rotary joint.
Figure 4B:
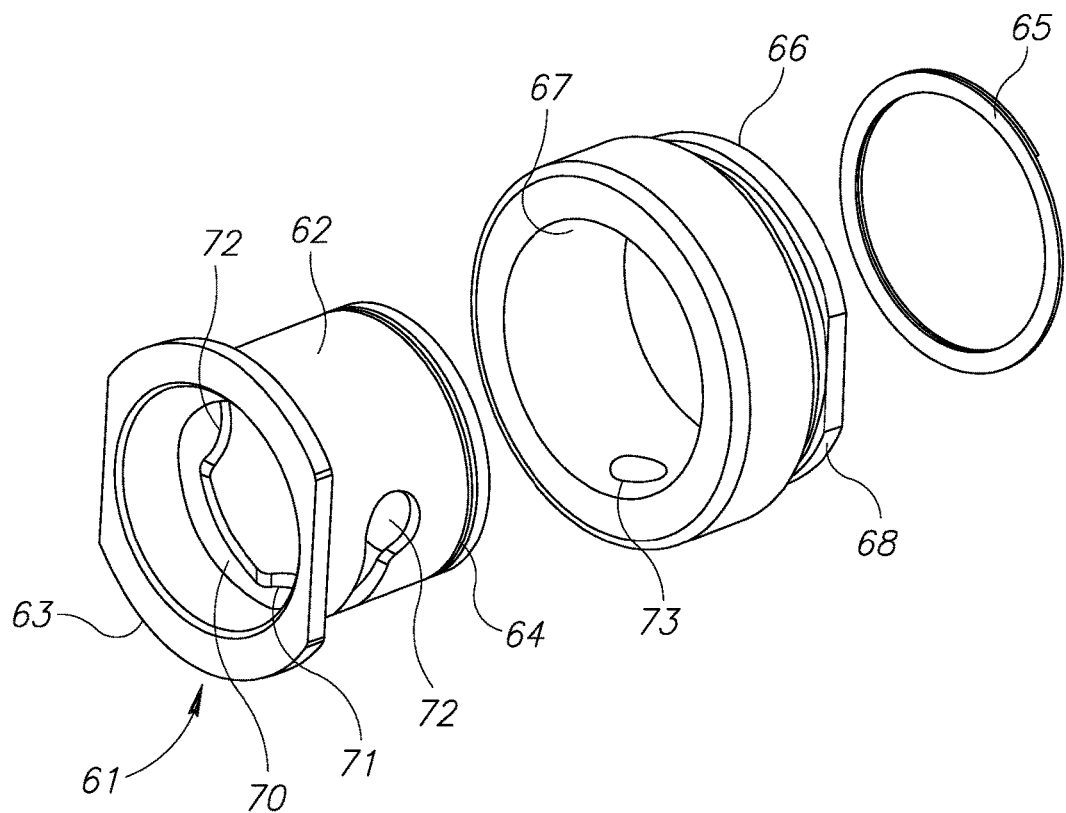
FIG. 4b is an exploded view of the rotary joint.

As shown above, the primary handset 11 is connected to an umbilical connection 12 for connection to a base station. When an auxiliary attachment is connected to the primary handset 11, it may be difficult to comfortably position the apparatus while holding the handle due to the position of the umbilical connection 12 immediately behind the handle 18. To overcome any difficulty, in the present example the primary handset is connected to the umbilical connection via a rotary joint 60, shown in FIGS. 4a to 4d. As shown in FIG. 4a, the umbilical connection 12 has a flexible hose section 12a and a curved, rigid or semi-rigid end part 12b. The primary handset 11 has a rearwardly extending projection 11a of about the same diameter as end part 12b. The rotary joint 60 comprises a first part 61, which has a generally cylindrical section 62 having a flange 63 at one end to engage the end part 12b, and a groove 64 disposed towards the other end to receive a ring clip 65. The rotary joint has a second part 66 having a generally annular shape, with an internal bore 67 shaped to receive the cylindrical portion 62 and a handset connector part 68 to connect to the projection 11a.

Figure 4C:
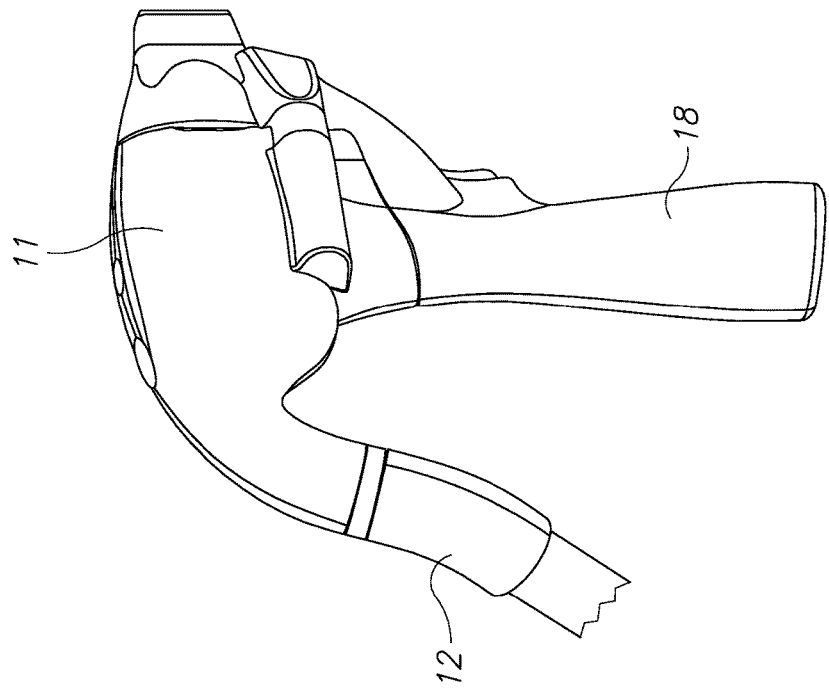
FIG. 4c is a perspective view of a primary handset and auxiliary attachment with the umbilical connection in a first position.
Figure 4D:
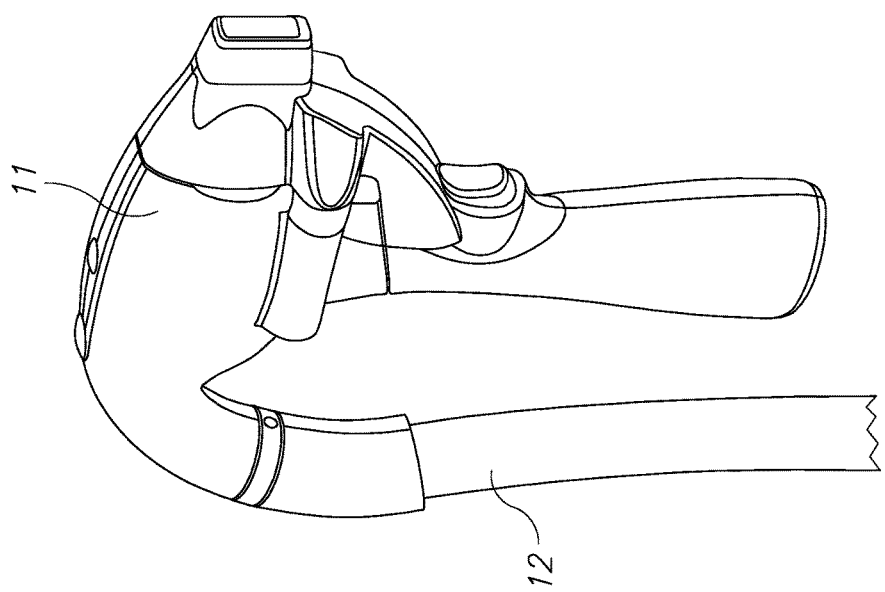
FIG. 4d is a view similar to FIG. 4c showing the umbilical connection in a second position.

The rotary joint 60 enables the first and second parts 61, 66 to be in one of several offset latched positions. A groove 70 extends circumferentially of the cylindrical part 62, connecting larger circular cutouts, a central cutout 71 and offset cutouts 72. In this example the offset cutouts are each offset by 90° around the circumference of the cylindrical part 62 from the central cutout 71. A projection 73 extends inwardly of the bore 67, and is dimensioned to be received in the cutouts 71, 72. When the projection 73 is in one of the cutouts 71, 72, the two parts of the rotary joint 60 are held in a latched position relative to one another. By rotating the handset 11 and end part 12b, the cylindrical portion can be caused to slightly deform, allowing the projection to move to another cutout 71,71, where it will once again be latched in place. FIG. 4c shows the umbilical connection latched in a central position, with projection 73 in central cutout 71. FIG. 4d shows the umbilical connection 12 rotated to the left, such that projection 73 will be in one of the offset cutouts 72, latched in a position away from the handle 18.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

Meanings of technical and scientific terms used herein are to be commonly understood as by one of ordinary skill in the art to which the invention belong, unless otherwise defined.

The invention claimed is:

1. A laser treatment apparatus comprising; a primary handset and an auxiliary handset, the primary handset being connectable to the auxiliary handset, the primary handset having a laser source, a primary heat exchanger and a main cooling circuit to provide cooling fluid to the primary heat exchanger to cool the laser source, the cooling circuit having a circuit connection for engagement with the auxiliary handset;
   wherein the circuit connection comprises a fluid connection for connection to an auxiliary cooling circuit within the auxiliary handset;
   wherein the auxiliary cooling circuit includes a secondary heat exchanger; and
   wherein a one-way loop valve causes cooling fluid to flow in the main cooling circuit within the primary handset when no auxiliary handset is attached and to divert flow of cooling fluid to the heat exchanger in the auxiliary handset when the auxiliary handset is connected to the primary handset.

2. The laser treatment apparatus of claim 1, wherein the auxiliary handset includes a tip window to transmit light from the laser source through the tip window.

3. The laser treatment apparatus according to claim 2, wherein the auxiliary cooling circuit of the auxiliary handset cools the tip window.

4. A laser treatment apparatus according to claim 1 comprising one or more pumps to pump cooling fluid around the one or more of the main and the auxiliary cooling circuit.

* * * * *